United States Patent
Shin et al.

(10) Patent No.: US 9,629,844 B2
(45) Date of Patent: Apr. 25, 2017

(54) STABILIZED PEMETREXED FORMULATION

(71) Applicant: CJ HEALTHCARE CORPORATION, Seoul (KR)

(72) Inventors: Myung Jin Shin, Seoul (KR); Hong Chul Jin, Seongnam-si (KR); Young Joon Park, Seoul (KR); Nak Hyun Choi, Yongin-si (KR); Ha Yong Choi, Yongin-si (KR)

(73) Assignee: CJ HEALTHCARE CORPORATION, Seoul (KR)

( * ) Notice: Subject to any disclaimer, the term of this patent is extended or adjusted under 35 U.S.C. 154(b) by 0 days.

(21) Appl. No.: 14/889,749

(22) PCT Filed: May 8, 2014

(86) PCT No.: PCT/KR2014/004105
§ 371 (c)(1),
(2) Date: Nov. 6, 2015

(87) PCT Pub. No.: WO2014/182093
PCT Pub. Date: Nov. 13, 2014

(65) Prior Publication Data
US 2016/0120867 A1    May 5, 2016

(30) Foreign Application Priority Data
May 8, 2013 (KR) .................. 10-2013-0052083

(51) Int. Cl.
| | | |
|---|---|---|
| A61K 31/519 | (2006.01) | |
| A61K 9/00 | (2006.01) | |
| A61K 47/12 | (2006.01) | |
| A61K 47/18 | (2017.01) | |
| A61K 31/198 | (2006.01) | |
| A61K 9/08 | (2006.01) | |
| A61K 47/02 | (2006.01) | |
| A61K 47/20 | (2006.01) | |

(52) U.S. Cl.
CPC .......... *A61K 31/519* (2013.01); *A61K 9/0019* (2013.01); *A61K 9/08* (2013.01); *A61K 31/198* (2013.01); *A61K 47/02* (2013.01); *A61K 47/12* (2013.01); *A61K 47/183* (2013.01); *A61K 47/20* (2013.01)

(58) Field of Classification Search
None
See application file for complete search history.

(56) References Cited

U.S. PATENT DOCUMENTS

| | | |
|---|---|---|
| 5,344,932 A | 9/1994 | Taylor |
| 6,686,365 B2 | 2/2004 | Riebesehl et al. |
| 9,265,832 B2 | 2/2016 | Park et al. |
| 2003/0216416 A1 | 11/2003 | Chelius et al. |
| 2009/0181990 A1 | 7/2009 | Patel et al. |
| 2011/0201631 A1 | 8/2011 | Kocherlakota et al. |

FOREIGN PATENT DOCUMENTS

| | | | |
|---|---|---|---|
| EP | 0 434 426 A1 | 6/1991 | |
| EP | 1 265 612 B1 | 5/2004 | |
| GB | WO 2012015810 A2 * | 2/2012 | ............... A61K 9/08 |
| JP | 5934448 B2 | 6/2016 | |
| KR | 10-0774366 | 3/2003 | |
| KR | 10-2007-0028331 | 3/2007 | |
| KR | 10-1069128 | 9/2011 | |
| KR | 10-1260636 | 5/2013 | |
| WO | 01/56575 A1 | 8/2001 | |
| WO | 2012/015810 A2 | 2/2012 | |
| WO | 2012/121523 A2 | 9/2012 | |
| WO | 2013/179248 A1 | 12/2013 | |

OTHER PUBLICATIONS

Allen, L. et al "Ansel's Pharmaceutical Dosage Forms and Drug Delivery Systems," Baltimore, Lippincott 2005, pp. 117 and 120.*
The United States Pharmacopeia, USP 35—The National Formulary, vol. 2, p. 2069 (3 pages) (May 1, 2012).

* cited by examiner

*Primary Examiner* — Heidi Reese
(74) *Attorney, Agent, or Firm* — Seed IP Law Group LLP

(57) ABSTRACT

The present invention relates to a stabilized pemetrexed formulation, and more specifically, to a stabilized pemetrexed formulation comprising acetylcysteine as an antioxidant and sodium citrate as a buffering agent. Additionally, the present invention relates to a pemetrexed formulation filled in a sealed container, comprising pemetrexed or a pharmaceutically acceptable salt thereof as an active ingredient, wherein the oxygen gas content within the headspace of the container is 3 v/v % or less.

7 Claims, 1 Drawing Sheet

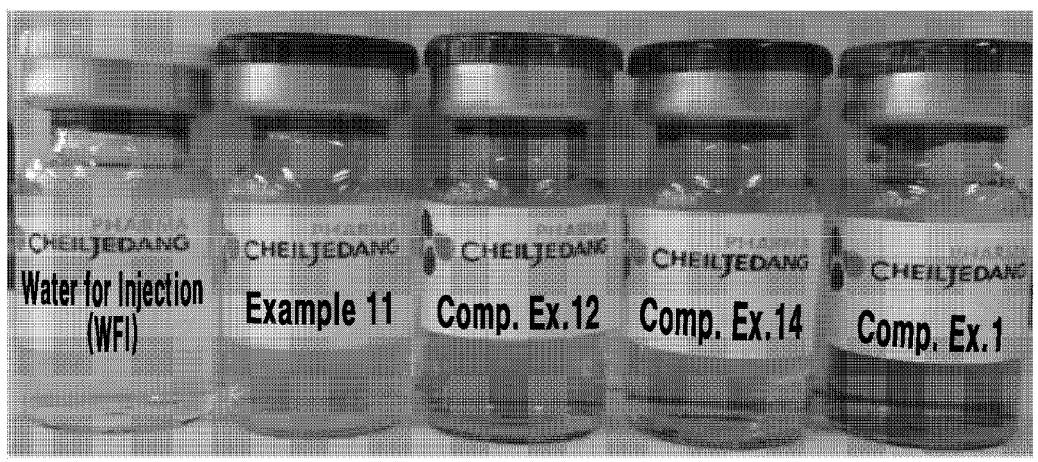

STABILIZED PEMETREXED FORMULATION

TECHNICAL FIELD

The present invention relates to a stabilized pemetrexed formulation, and more specifically, to a stabilized pemetrexed formulation containing acetylcysteine as an antioxidant and sodium citrate as a buffering agent and to a preparation method thereof. Additionally, the present invention relates to a pemetrexed formulation filled in a sealed container, comprising pemetrexed or a pharmaceutically acceptable salt thereof as an active ingredient, wherein the oxygen content within the headspace of the container is 3 v/v % or less.

BACKGROUND ART

Compounds having particular antifolate activities are known as chemotherapeutic agents. U.S. Pat. No. 5,344,932 describes a method for manufacturing particularly substituted pyrrolo[2,3-d]pyrimidine-based antifolate derivatives including pemetrexed, and European Patent Application Publication No. 0434426 discloses a series of 4-hydroxy-pyrrolo[2,3-d]pyrimidine-L-glutamic acid derivatives.

Pemetrexed, a 5-substituted pyrrolo[2,3-d]pyrimidine, is a multi-targeted antifolate exhibiting anticancer activity by suppressing the activities of metabolites involved in folate metabolism in various kinds of cancer including non-small cell lung cancer.

Pemetrexed has been known to target thymidylate synthase (TS) and dihydrofolate reductase (DHFR) when it is activated into polyglutamate derivatives by folylpolyglutamate synthetase (FPGS), after it is introduced into the cells via reduced folate carrier (RFC), which is a major intracellular transport channel for folates.

Pemetrexed, already developed in the brand name of ALIMTA™, is currently available on the market as an agent for treating malignant pleural mesothelioma and non-small cell lung cancer (Physicians' Desk Reference, 60th ed., pp. 1722-1728 (2006)). ALIMTA™ is currently sold in the market in the form of a lyophilized formulation (100 mg or 500 mg), which requires reconstitution prior to administration, i.e., when it is administered to a patient, it should be reconstituted with 0.9% sodium chloride solution and finally diluted with 0.9% sodium chloride solution (final concentration of 0.25 mg/mL).

The manufacturing process for formulations of the type of lyophilized powder is complex and its processing requires high cost. Additionally, there is a risk of microbial contamination during the reconstitution of lyophilized formulations, and pharmacists, doctors, nurses, etc. who are involved in preparing medicine are highly likely to be exposed to cell-destroying materials. Accordingly, in the case of a cytotoxic anticancer agent such as pemetrexed, it is necessary to develop a ready-to-use liquid formulation which can be stored for a long period of time, rather than a lyophilized formulation.

In many cases, the problem in liquid formulations lies in their instability during storage. Due to the instability, many injectable formulations are used in the form of a lyophilized formulation, which is dissolved immediately before injection. In the case of pemetrexed or a pharmaceutically acceptable salt thereof, which has been provided in the form of a lyophilized formulation, the manufacture in the form of an aqueous solution may lead to an increase in the amount of unknown impurities and thus a long-term storage at room temperature may not be possible. For stability reasons, they have still been used in the form of lyophilized formulations in clinical studies.

Several formulations have been suggested to overcome the problems described above. For example, U.S. Pat. No. 6,686,365 (Korean Patent Application Publication No. 2002-0081293) discloses a stable liquid pemetrexed formulation, which is a liquid pemetrexed formulation containing a therapeutically effective amount of pemetrexed, an effective amount of an antioxidant, and a pharmaceutically acceptable excipient, wherein the antioxidant is selected from the group consisting of monothioglycerol, L-cysteine, and thioglycolic acid.

However, the above patent reportedly has a problem in that precipitation occurs during the progress of long-term storage stability test at 25° C., and it thus cannot secure stability for the desired period (International Patent Publication No. WO 2012/015810). Until today, no liquid pemetrexed formulation having long-term storage stability has been experimentally or commercially successful. The present inventors prepared a liquid formulation comprising pemetrexed using L-cysteine, the antioxidant described above, performed its stability test, and found that problems, such as changes in characteristics such as discoloration, etc., increase in impurities, decrease in pH, etc., occurred from the second week under stress testing conditions. Additionally, the present inventors prepared liquid formulations comprising pemetrexed using more than sixty stabilizers including ascorbic acid, sodium thiosulfate, butylated hydroxyanisole, propyl gallate, EDTA, L-methionine, acetylcysteine, etc. However, all of these formulations did not have the appropriate stability.

DISCLOSURE

Technical Problem

The present inventors, while endeavoring to overcome the stability problem present in pemetrexed-comprising liquid formulations, discovered that a pemetrexed formulation which is capable of effectively lowering or excluding the generation of pemetrexed isomer as an impurity and unknown impurities and maintaining high stability in the state of a transparent solution without precipitates during the storage period can be manufactured by using both acetylcysteine as an antioxidant and sodium citrate as a buffering agent together, thereby completing the present invention. Additionally, the present inventors confirmed that, in the case of large-scale production of the above formulation, the stability of the formulation can be secured by controlling the empty space in the upper part of a container, i.e., the oxygen content within the headspace, thereby completing the present invention.

Technical Solution

An object of the present invention is to provide a stabilized pemetrexed formulation.

Advantageous Effects of the Invention

The present invention can provide a pemetrexed formulation with improved administration convenience and stability, which can be easily manufactured from the commercial aspect and prevent microbial contamination accompanied during lyophilization or reconstitution. Additionally, since the pemetrexed formulation of the present invention contains acetylcysteine as an antioxidant and sodium citrate as a buffering agent, a stabilized pemetrexed formulation to satisfy the standard requirements without abnormal characteristics, such as discoloration or precipitation, compared to the conventional pemetrexed-comprising liquid formulation for injection, can be provided. Additionally, the present invention can prevent oxidation that may occur within the headspace, by controlling the oxygen content within the headspace, thereby providing a more stable pemetrexed formulation.

BRIEF DESCRIPTION OF THE DRAWINGS

FIG. 1 shows an image illustrating comparative features in stability between the conventional pemetrexed-comprising liquid formulations for injection (Comparative Examples 1, 12, and 14) and the pemetrexed-comprising liquid formulation for injection according to the present invention (Example 11) after a 4-week stress stability test (60° C./80%). For comparison purposes, the properties of the water for injection are also shown.

BEST MODE

In order to accomplish the above object, the present invention provides a pemetrexed formulation comprising pemetrexed or a pharmaceutically acceptable salt thereof as an active ingredient, N-acetyl-L-cysteine, and sodium citrate.

In the present invention, the concentration ratio of the pemetrexed or a pharmaceutically acceptable salt thereof, N-acetyl-L-cysteine, and sodium citrate may be 1 to 30:0.15 to 2.0:1.0 to 15.0.

Preferably, the concentration ratio of the pemetrexed or a pharmaceutically acceptable salt thereof, N-acetyl-L-cysteine, and sodium citrate may be 1 to 30:1.5:1.0 to 15.0.

In the present invention, the formulation may be a liquid formulation storable in the state of a solution.

In the present invention, the formulation may be a liquid formulation for injection filled in a sealed, ready-to-use container.

However, the scope of the present invention may not necessarily be limited to the liquid formulations for injection, but may include other types of liquid formulations and non-liquid formulations that can be constituted based on the common knowledge of one of ordinary skill in the art or the method conventionally used in the art.

Additionally, the present invention provides a pemetrexed formulation filled in a sealed container comprising pemetrexed or a pharmaceutically acceptable salt thereof as an active ingredient, wherein the formulation comprises an oxygen gas content of 3 v/v % or less within the headspace of the container, relative to the total volume of the headspace.

In the present invention, preferably, the formulation may further comprise N-acetyl-L-cysteine and sodium citrate.

In the present invention, the concentration ratio of the pemetrexed or a pharmaceutically acceptable salt thereof, N-acetyl-L-cysteine, and sodium citrate may be 1 to 30:0.15 to 2.0:1.0 to 15.0.

Preferably, the concentration ratio of the pemetrexed or a pharmaceutically acceptable salt thereof, N-acetyl-L-cysteine, and sodium citrate may be 1 to 30:1.5:1.0 to 15.0.

In the present invention, the formulation may be a liquid formulation storable in the state of a solution.

In the present invention, the formulation may be a liquid formulation for injection filled in a sealed, ready-to-use container.

In the present invention, the formulation may be one in which the oxygen gas content was adjusted to a level of 3 v/v % or less by substituting the oxygen gas within the headspace of the container with an inert gas.

In the present invention, the inert gas may be nitrogen gas or argon gas, but is not limited thereto.

The present invention is described in detail herein below.

There are various kinds of antioxidants that may generally be used for stabilizing formulations, and examples of these antioxidants may include parahydroxybenzoic acid ester derivatives, alcohols, phenol derivatives, thimerosal, acetic anhydride, sodium carboxylate, lauryl sulfate, antioxidants, sulfide compounds, sulfite, cystine, cysteine, cysteamine, amino acids, and organic acids such as ascorbic acid, retinol, tocopherol, butylated hydroxyanisole, etc.

Additionally, Korean Patent No. 10-0774366 discloses N-acetyl amino acids as antioxidants for paclitaxel, and Korean Patent Publication No. 10-2007-0028331 discloses monothioglycerol and ethylenediaminetetraacetic acid as antioxidants for a composition comprising diclofenac.

In the present invention, experiments on the stabilization of pemetrexed formulations for injection were performed using the antioxidants described above. As a result, it was confirmed that the general antioxidants described above have problems in that their daily doses are limited, especially when they are used as excipients (antioxidants) instead of active ingredients for injectable formulations, and also that the antioxidants alone cannot improve stability of the formulations. Additionally, when ascorbic acid, lactic acid, etc., which are often used in the conventional injections, were used, the injection liquids showed acid instability, such as partial discoloration and/or precipitation, etc. (Experimental Examples 1 and 2).

Surprisingly, however, the present inventors discovered that when a composition comprising pemetrexed or a pharmaceutically acceptable salt thereof as an active ingredient was further comprised both acetylcysteine and sodium citrate together, the active ingredient did not undergo any substantial change and also no discoloration or generation of precipitates occurred under stress testing conditions (60° C./80%) for four weeks, thus confirming that the composition had the appropriate stability to meet the required acceptance criteria (Experimental Examples 1 and 2). Because both acetylcysteine and sodium citrate are generally used and their prices are cheap, they have commercial advantages.

The pemetrexed formulation of the present invention comprises pemetrexed or a pharmaceutically acceptable salt thereof as an active ingredient. The pemetrexed includes a pharmacologically effective drug, or one which is pharmacologically effective by an in vivo chemical or enzymatic method, and specifically, the pemetrexed drug itself and a pharmaceutically acceptable salt thereof may be used.

As used herein, the term "pemetrexed" refers to a compound having the name of 5-substituted pyrrolo[2,3-d]pyrimidine, and specifically, refers to a multi-targeted antifolate represented by Formula 1 exhibiting an anticancer effect in various kinds of cancer including non-small cell lung cancer, malignant pleural mesothelioma, etc.

[Formula 1]

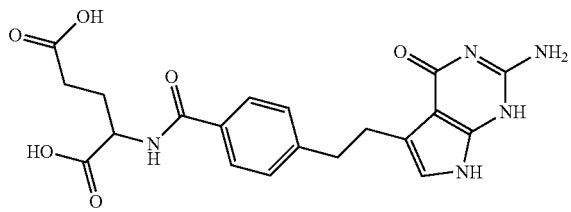

The pemetrexed exhibits anticancer effects by inhibiting the activities of metabolites involved in folate metabolism in various kinds of cancer including non-small cell lung cancer, malignant pleural mesothelioma, etc.

As used herein, the term "a pharmaceutically acceptable salt" refers to a salt manufactured according to a conventional method in the art, and the method is known to one of ordinary skill in the art. Specifically, the pharmaceutically acceptable salt may include salts derived from the pharmacologically or physiologically acceptable inorganic acids, organic acids, and bases below, but is not limited thereto. Examples of appropriate acids may include hydrochloric acid, bromic acid, hydrobromic acid, sulfuric acid, nitric acid, perchloric acid, fumaric acid, maleic acid, phosphoric acid, glycolic acid, lactic acid, salicylic acid, succinic acid, p-toluene sulfonic acid, tartaric acid, acetic acid, citric acid, methanesulfonic acid, formic acid, benzoic acid, malonic acid, naphthalene-2-sulfonic acid, benzenesulfonic acid, etc. Examples of salts derived from appropriate bases may include alkali metals, for example, sodium, or potassium, alkali earth metals, for example, magnesium, but are not limited thereto.

As used herein, the term "acetylcysteine" refers to a compound having the name of N-acetyl-L-cysteine (NAC, $C_5H_9NO_3S$, CAS number 616-91-1), and refers to a compound used as an antioxidant of the pemetrexed formulation of the present invention. In the present invention, "acetylcysteine" and "N-acetyl-L-cysteine" are interchangeably used.

Acetylcysteine as an antioxidant is described in U.S. Pharmacopeia 35 (National Formulary 10, p 2069). Acetylcysteine is a precursor of L-cysteine, one of the amino acids present in foods, where cysteine is oxidized and easily denatured into an insoluble material, whereas acetylcysteine is stable and hardly denatured, and is thus suitable for oral administration or intravenous injection.

As used herein, the term "sodium citrate" refers to a sodium salt of citric acid, and refers to a compound being used as a buffering agent in the pemetrexed formulation of the present invention.

The present invention is characterized in that it can provide a pemetrexed formulation enabling long-term pharmaceutically stable storage of pemetrexed at a temperature in the range of from 1° C. to 30° C. by using both acetylcysteine as an antioxidant and sodium citrate as a buffering agent together.

In the pemetrexed formulation of the present invention, the concentration ratio of the pemetrexed or a pharmaceutically acceptable salt thereof, N-acetyl-L-cysteine, and sodium citrate is preferably 1 to 30:0.15 to 2.0:1.0 to 15.0, and more preferably, the concentration ratio is 1 to 30:1.5:1.0 to 15.0. In particular, the concentration unit may be mg/mL, respectively. The pemetrexed formulation having a concentration ratio different from the above range was shown to increase the generation of impurities beyond the acceptance criteria along with the storage time (Experimental Example 1).

In the present invention, the pemetrexed formulation may comprise a pharmaceutically acceptable carrier and a pH adjusting agent.

In the present invention, the pemetrexed formulation may preferably be a liquid formulation storable in the state of a solution, and more preferably, may be a liquid formulation for injection filled in a sealed, ready-to-use container.

In the present invention, when the pemetrexed formulation is a liquid formulation for injection, the pharmaceutically acceptable carrier can be water for injection.

In the present invention, the pH of the pemetrexed liquid formulation for injection may preferably be in the range of from about 6.0 to about 8.0, and more preferably, from about 7.2 to about 7.8. The pH of solutions may possibly be adjusted using an acid such as hydrochloric acid or a base such as sodium hydroxide.

The pemetrexed formulation of the present invention may not necessarily comprise other additives in addition to acetylcysteine and sodium citrate described above, but may further comprise a pharmaceutically acceptable excipient. Examples of the pharmaceutically acceptable excipient may include known additives, such as lactose, dextrose, cyclodextrine and a derivative thereof, sucrose, glycerol, sodium carbonate, etc., and preferably, sodium chloride, mannitol, etc.

Additionally, the present invention provides a method for preparing a stabilized pemetrexed formulation comprising mixing pemetrexed or a pharmaceutically acceptable salt thereof, N-acetyl-L-cysteine, and sodium citrate.

In the present invention, the mixing concentration ratio of the pemetrexed or a pharmaceutically acceptable salt thereof, N-acetyl-L-cysteine, and sodium citrate may be 1 to 30:0.15 to 2.0:1.0 to 15.0.

Preferably, the mixing concentration ratio of the pemetrexed or a pharmaceutically acceptable salt thereof, N-acetyl-L-cysteine, and sodium citrate may be 1 to 30:1.5:1.0 to 15.0.

In preparing the formulation of the present invention, in order to maintain a condition with a low-oxygen level, the formulation is purged using an inert gas such as nitrogen or argon and then filtered for sterilization.

Additionally, the stabilized pemetrexed formulation of the present invention may be packaged in an appropriate container known in the art, for example, glass vials, glass bottles, cartridges, pre-filled syringes, or the like, and preferably glass vials. The injectable liquid formulation of pemetrexed according to the present invention is dispensed in a previously washed and sterilized container, and the container is sealed with a teflon stopper whose surface is not reactive with the liquid formulation.

In particular, the space between the liquid formulation for injection and the stopper may be filled with an inert gas, when necessary. The stopper may be attached thereto using a crimper and the vials filled with the liquid formulation for injection may be sterilized by heating, when necessary.

Additionally, the present invention relates to a pemetrexed formulation containing pemetrexed or a pharmaceutically acceptable salt thereof as an active ingredient, and provides a pemetrexed formulation in which the oxygen content within the headspace of the container was controlled to a range of 3 v/v % or less.

As used herein, the term "headspace" refers to an upper space within a sealed container remaining after the pemetrexed formulation has been filled. The volume of the headspace may vary depending on the entire inner volume of the container to be used and the amount of pemetrexed being filled thereinto.

As used herein, the term "the oxygen gas content within the headspace" refers to the volume ratio being accounted for the volume of the space occupied by oxygen gas to the entire volume of the headspace. Accordingly, the % unit representing the oxygen content refers to volume (v/v) %.

In the present invention, the oxygen gas content within the headspace may be 3 v/v % or less, i.e., in the range of from 0 v/v % to 3 v/v %, and specifically, from 0.001 v/v % to 3 v/v %. In an exemplary embodiment, the oxygen gas content within the headspace may be 3 v/v %.

The container to be used in the present invention is the same as described above, and is preferably a glass vial.

In the present invention, preferably, the formulation may further comprise N-acetyl-L-cysteine and sodium citrate. In particular, the preferable concentration ratio of the pemetrexed or a pharmaceutically acceptable salt thereof, N-acetyl-L-cysteine, and sodium citrate is the same as explained above.

Preferably, the formulation of the present invention may be a liquid formulation storable in the state of a solution, and in particular, may be a liquid formulation for injection filled in a sealed, ready-to-use container.

In the present invention, control of the oxygen gas content may be performed by substituting the oxygen within the headspace of the container with an inert gas. The inert gas may be nitrogen or argon, but is not limited thereto.

In the present invention, in order to minimize the problem of generation of impurities by the oxygen within the headspace of the container, during the manufacture of the pemetrexed formulation comprising pemetrexed or a pharmaceutically acceptable salt thereof as an active ingredient filled in a sealed container, especially during the large-scale production of the pemetrexed formulation, the oxygen gas content within the headspace was controlled to a level of 3 v/v % or less, and thereby the stability of the pemetrexed formulation was significantly improved (Experimental Example 1 and Table 10).

In the present invention, as described above, the oxidation that may occur within the headspace can be prevented using the method of controlling the oxygen gas content within the headspace, and more specifically, using a method of substituting the oxygen therein with nitrogen. According to the present invention, the manufacture of a cheap and stabilized pemetrexed-comprising formulation for injection can be scaled up to a commercial level using an automated system widely used at present, thereby enabling the large-scale production of the formulation.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Examples 1 to 14

Preparation of the Pemetrexed-Comprising Solutions for Injection, Comprising Acetylcysteine as an Antioxidant and Sodium Citrate as a Buffering Agent at Different Contents After dissolving 2.5 g of D-mannitol in 100 mL of water for injection, acetylcysteine and sodium citrate were sequentially added to the solution at concentrations shown in Table 1 below and dissolved completely. 2.5 g of pemetrexed was slowly added to the resultant (3.0 g of pemetrexed was slowly added in Example 14), and the mixed solution was stirred until the solution became transparent. Then, its pH was adjusted to that shown in Table 1 using an aqueous solution of hydrochloric acid or sodium hydroxide. The solution was aseptically filtered via a sterile 0.22 μm filter (membrane filter) in a clean room. The thus-obtained solution was filled into a sealable container being washed and sterile, after purging using nitrogen gas.

The compositions and pH of the obtained pemetrexed-comprising solutions for injection are shown in Table 1 below.

TABLE 1

| | Conc. of active ingredient (mg/mL) | Antioxidant | Conc. of antioxidant (mg/mL) | Buffering agent | Conc. of buffering agent (mg/mL) | pH |
|---|---|---|---|---|---|---|
| Ex. 1 | 25 | acetylcysteine | 0.15 | sodium citrate | 2.0 | 7.3 |
| Ex. 2 | 25 | acetylcysteine | 0.3 | sodium citrate | 2.0 | 7.2 |
| Ex. 3 | 25 | acetylcysteine | 0.5 | sodium citrate | 1.0 | 7.2 |
| Ex. 4 | 25 | acetylcysteine | 0.5 | sodium citrate | 2.0 | 7.2 |
| Ex. 5 | 25 | acetylcysteine | 0.5 | sodium citrate | 3.0 | 7.3 |
| Ex. 6 | 25 | acetylcysteine | 0.5 | sodium citrate | 4.0 | 7.4 |
| Ex. 7 | 25 | acetylcysteine | 0.5 | sodium citrate | 5.0 | 7.4 |
| Ex. 8 | 25 | acetylcysteine | 1.0 | sodium citrate | 2.0 | 7.4 |
| Ex. 9 | 25 | acetylcysteine | 1.5 | sodium citrate | 1.0 | 7.5 |
| Ex. 10 | 25 | acetylcysteine | 1.5 | sodium citrate | 2.0 | 7.5 |
| Ex. 11 | 25 | acetylcysteine | 1.5 | sodium citrate | 5.0 | 7.5 |
| Ex. 12 | 25 | acetylcysteine | 1.5 | sodium citrate | 15.0 | 7.5 |
| Ex. 13 | 25 | acetylcysteine | 2.0 | sodium citrate | 5.0 | 7.4 |
| Ex. 14 | 30 | acetylcysteine | 1.5 | sodium citrate | 5.0 | 7.4 |

Examples 15 and 16

Preparation of Pemetrexed-Comprising Solutions for Injection of the Present Invention According to pH Change After dissolving 2.5 g of D-mannitol in 100 mL of water for injection, acetylcysteine and sodium citrate were sequentially added to the solution at concentrations shown in Table 2 below and dissolved completely. 2.5 g of pemetrexed was slowly added to the resultant, and the mixed solution was stirred until the solution became transparent. Then, its pH was adjusted to that shown in Table 2 using an aqueous solution of hydrochloric acid or sodium hydroxide. The solution was aseptically filtered via a sterile 0.22 μm filter (membrane filter) in a clean room. The thus-obtained solution was filled into a sealable container being washed and sterile, after purging using nitrogen gas.

The compositions and pH of the obtained pemetrexed-comprising solutions for injection are shown in Table 2 below.

TABLE 2

|  | Conc. of active ingredient (mg/mL) | Antioxidant | Conc. of antioxidant (mg/mL) | Buffering agent | Conc. of buffering agent (mg/mL) | pH |
|---|---|---|---|---|---|---|
| Ex. 15 | 25 | acetylcysteine | 1.5 | sodium citrate | 5.0 | 6.8 |
| Ex. 16 | 25 | acetylcysteine | 1.5 | sodium citrate | 5.0 | 7.2 |

Examples 17 to 20

Preparation of Pemetrexed-Comprising Solution for Injection According to the Oxygen Content within Headspace After dissolving 2.5 g of D-mannitol in 100 mL of water for injection, acetylcysteine and sodium citrate were sequentially added to the solution at concentrations shown in Table 3 below and dissolved completely. 2.5 g of pemetrexed was slowly added to the resultant, and the mixed solution was stirred until the solution became transparent. Then, its pH was adjusted to that shown in Table 3 using an aqueous solution of hydrochloric acid or sodium hydroxide.

The solution was aseptically filtered via a sterile 0.22 μm filter (membrane filter) in a clean room. The thus-obtained solution was filled into a sealable container being washed and sterile, after purging using nitrogen gas until the oxygen content within the headspace to those shown in Table 3.

The compositions and oxygen gas content within the headspace of the obtained pemetrexed-comprising solutions for injection are shown in Table 3 below.

TABLE 3

|  | Conc. of active ingredient (mg/mL) | Antioxidant | Conc. of antioxidant (mg/mL) | Buffering agent | Conc. of buffering agent (mg/mL) | pH | Oxygen gas content within the headspace (v/v %) |
|---|---|---|---|---|---|---|---|
| Ex. 17 | 25 | acetylcysteine | 1.5 | sodium citrate | 5.0 | 7.4 | 3 |
| Ex. 18 | 25 | acetylcysteine | 1.5 | sodium citrate | 5.0 | 7.4 | 5 |
| Ex. 19 | 25 | acetylcysteine | — | sodium citrate | — | 7.4 | 3 |
| Ex. 20 | 25 | acetylcysteine | — | sodium citrate | — | 7.4 | 5 |

Comparative Examples 1 to 8

Preparation of Pemetrexed-Comprising Solution for Injection According to the Type of Antioxidants Pemetrexed-comprising solutions were prepared according to the compositions and contents in Table 4 below, in the same manner as in Example 1. In Comparative Example 1, the solution was prepared using only the water for injection as a carrier without adding any antioxidant.

TABLE 4

|  | Conc. of active ingredient (mg/mL) | Type of antioxidant | Conc. of antioxidant (mg/mL) | pH |
|---|---|---|---|---|
| Comp. Ex. 1 | 25 | — | — | 7.5 |
| Comp. Ex. 2 | 25 | ascorbic acid | 0.3 | 6.5 |
| Comp. Ex. 3 | 25 | sodium thiosulfate | 0.3 | 7.5 |
| Comp. Ex. 4 | 25 | butylated hydroxyanisole | 0.3 | 9.9 |
| Comp. Ex. 5 | 25 | propyl gallate | 0.3 | 9.5 |
| Comp. Ex. 6 | 25 | EDTA | 0.3 | 6.8 |
| Comp. Ex. 7 | 25 | L-cysteine | 0.3 | 7.5 |
| Comp. Ex. 8 | 25 | L-methionine | 0.3 | 7.4 |

Comparative Examples 9 to 14

Preparation of Pemetrexed-Comprising Solution for Injection According to the Type of Antioxidants and to the Presence of Buffering Agents Pemetrexed-comprising solutions were prepared according to the compositions and contents shown in Table 5 below, in the same manner as in Example 1.

TABLE 5

| | Conc. of active ingredient (mg/mL) | Type of antioxidant | Conc. of antioxidant (mg/mL) | Buffering agent | Conc. of buffering agent (mg/mL) | pH |
|---|---|---|---|---|---|---|
| Comp. Ex. 9 | 25 | — | — | sodium citrate | 1.5 | 7.4 |
| Comp. Ex. 10 | 25 | — | — | sodium citrate | 2.0 | 7.3 |
| Comp. Ex. 11 | 25 | acetylcysteine | 0.5 | — | — | 7.2 |
| Comp. Ex. 12 | 25 | acetylcysteine | 1.5 | — | — | 7.5 |
| Comp. Ex. 13 | 25 | L-cysteine | 0.5 | — | — | 7.5 |
| Comp. Ex. 14 | 25 | L-cysteine | 1.5 | — | — | 7.5 |

Comparative Examples 15 to 17

Preparation of Pemetrexed-Comprising Solution for Injection According to the Type of Buffering Agents Pemetrexed-comprising solutions were prepared according to the compositions and contents shown in Table 6 below, in the same manner as in Example 1.

TABLE 6

| | Conc. of active ingredient (mg/mL) | Type of antioxidant | Conc. of antioxidant (mg/mL) | Buffering agent | Conc. of buffering agent (mg/mL) | pH |
|---|---|---|---|---|---|---|
| Comp. Ex. 15 | 25 | acetylcysteine | 1.5 | sodium acetate | 5.0 | 7.4 |
| Comp. Ex. 16 | 25 | acetylcysteine | 1.5 | sodium hydrogen phosphate | 5.0 | 7.5 |
| Comp. Ex. 17 | 25 | acetylcysteine | 1.5 | potassium dihydrogen phosphate | 5.0 | 7.5 |

EXPERIMENTAL EXAMPLE

Stability Test

Stability tests were performed for compositions prepared in Examples 1 to 20 and Comparative Examples 1 to 17 under stress testing conditions (60° C./80%) for four weeks. Among them, for compositions prepared in Example 11 and Comparative Examples 1, 12, and 14, stability tests were performed under accelerated conditions (40° C./70%) for four months as well. Evaluation of stability was performed by measuring the content of pemetrexed remaining in the aqueous solution and the content of impurities via a high performance liquid chromatographic (HPLC) method under conditions described in Table 7 below.

TABLE 7

| Column | C8, 150 mm × 4.6 mm, 3.5 μm |
|---|---|
| Detector | UV spectrophotometer (250 nm) |
| Mobile phase | Gradient method |
| | mobile phase A - acetate buffer:acetonitrile (97:3) |
| | mobile phase B - acetate buffer:acetonitrile (87.5:12.5) |
| | acetate buffer (0.03 mol/L, pH 5.5) - 3.4 mL of acetic acid is added to 2 L of water, stirred, and the mixture is adjusted to have a pH of 5.5 with 50% of sodium hydroxide |
| Flow rate | 1 mL/min |
| Column temp. | 35° C. |
| Time for analysis | 55 min |

Experimental Example 1

Stability Test Under Stress Testing Conditions (60° C./80%, 4 Week Evaluation of Stability)

The results of stability tests performed under stress testing conditions as described above are shown in Tables 8 to 13.

Additionally, among the pemetrexed-comprising liquid formulations for injection prepared above, the images showing the comparative features in stability stress testing conditions (60° C./80%) between the pemetrexed-comprising liquid formulation for injection of the present invention prepared in Example 11 and the conventional pemetrexed-comprising liquid formulations for injection prepared in Comparative Examples 1, 12, and 14, are provided in FIG. 1. In particular, for comparison purposes, the appearance of water for injection is shown as well.

TABLE 8

| | Conc. of active ingredient (mg/mL) | Antioxidant | Conc. of antioxidant (mg/mL) | Buffering agent | Conc. of buffering agent (mg/mL) | pH | | Impurities (%) individual/total |
|---|---|---|---|---|---|---|---|---|
| Ex. 1 | 25 | acetylcysteine | 0.15 | sodium citrate | 2.0 | 7.3 | initial | 0.05/0.1 (colorless and transparent) |
| | | | | | | | week 2 | 0.09/0.3 (yellow) |
| | | | | | | | week 4 | 0.11/0.6 (yellow) |
| Ex. 2 | 25 | acetylcysteine | 0.3 | sodium citrate | 2.0 | 7.2 | initial | 0.07/0.1 (colorless and transparent) |
| | | | | | | | week 2 | 0.10/0.3 (pale yellow) |
| | | | | | | | week 4 | 0.12/0.6 (yellow) |
| Ex. 3 | 25 | acetylcysteine | 0.5 | sodium citrate | 1.0 | 7.2 | initial | 0.07/0.1 (colorless and transparent) |
| | | | | | | | week 2 | 0.10/0.1 (light pale yellow) |
| | | | | | | | week 4 | 0.11/0.4 (pale yellow) |
| Ex. 4 | 25 | acetylcysteine | 0.5 | sodium citrate | 2.0 | 7.2 | initial | 0.07/0.1 (colorless and transparent) |
| | | | | | | | week 2 | 0.10/0.1 (pale yellow) |
| | | | | | | | week 4 | 0.13/0.5 (pale yellow) |
| Ex. 5 | 25 | acetylcysteine | 0.5 | sodium citrate | 3.0 | 7.3 | initial | 0.07/0.1 (colorless and transparent) |
| | | | | | | | week 2 | 0.15/0.3 (pale yellow) |
| | | | | | | | week 4 | 0.10/0.4 (pale yellow) |
| Ex. 6 | 25 | acetylcysteine | 0.5 | sodium citrate | 4.0 | 7.4 | initial | 0.07/0.1 (colorless and transparent) |
| | | | | | | | week 2 | 0.10/0.2 (colorless and transparent) |
| | | | | | | | week 4 | 0.12/0.5 (pale yellow) |
| Ex. 7 | 25 | acetylcysteine | 0.5 | sodium citrate | 5.0 | 7.4 | initial | 0.07/0.1 (colorless and transparent) |
| | | | | | | | week 2 | 0.10/0.2 (colorless and transparent) |
| | | | | | | | week 4 | 0.12/0.5 (pale yellow) |
| Ex. 8 | 25 | acetylcysteine | 1.0 | sodium citrate | 2.0 | 7.4 | initial | 0.08/0.1 (colorless and transparent) |
| | | | | | | | week 2 | 0.11/0.2 (colorless and transparent) |
| | | | | | | | week 4 | 0.13/0.5 (colorless and transparent) |
| Ex. 9 | 25 | acetylcysteine | 1.5 | sodium citrate | 1.0 | 7.5 | initial | 0.08/0.1 (colorless and transparent) |
| | | | | | | | week 2 | 0.11/0.2 (colorless and transparent) |
| | | | | | | | week 4 | 0.10/0.3 (colorless and transparent) |

TABLE 8-continued

| | Conc. of active ingredient (mg/mL) | Antioxidant | Conc. of antioxidant (mg/mL) | Buffering agent | Conc. of buffering agent (mg/mL) | pH | | Impurities (%) individual/total |
|---|---|---|---|---|---|---|---|---|
| Ex. 10 | 25 | acetylcysteine | 1.5 | sodium citrate | 2.0 | 7.5 | initial | 0.08/0.1 (colorless and transparent) |
| | | | | | | | week 2 | 0.12/0.1 (colorless and transparent) |
| | | | | | | | week 4 | 0.12/0.3 (colorless and transparent) |
| Ex. 11 | 25 | acetylcysteine | 1.5 | sodium citrate | 5.0 | 7.5 | initial | 0.07/0.1 (colorless and transparent) |
| | | | | | | | week 2 | 0.10/0.1 (colorless and transparent) |
| | | | | | | | week 4 | 0.11/0.2 (colorless and transparent) |
| Ex. 12 | 25 | acetylcysteine | 1.5 | sodium citrate | 15.0 | 7.5 | initial | 0.07/0.1 (colorless and transparent) |
| | | | | | | | week 2 | 0.11/0.1 (colorless and transparent) |
| | | | | | | | week 4 | 0.11/0.2 (colorless and transparent) |
| Ex. 13 | 25 | acetylcysteine | 2.0 | sodium citrate | 5.0 | 7.4 | initial | 0.20/0.2 (colorless and transparent) |
| | | | | | | | week 2 | 0.25/0.4 (light pale yellow) |
| | | | | | | | week 4 | 0.25/0.6 (light pale yellow) |
| Ex. 14 | 30 | acetylcysteine | 1.5 | sodium citrate | 5.0 | 7.5 | initial | 0.11/0.1 (colorless and transparent) |
| | | | | | | | week 2 | 0.15/0.2 (colorless and transparent) |
| | | | | | | | week 4 | 0.15/0.3 (light pale yellow) |

As can be confirmed in the results of Table 8 above, when 1.5 mg/mL of acetylcysteine as an antioxidant and 1 mg/mL to 15 mg/mL of sodium citrate as a buffering agent were used together in the formulations, individual impurity was 0.2% or less while the total impurity was 1.0% or less during the four weeks' stability test period under stress testing conditions, thus showing excellent stability (Examples 9 to 12).

Additionally, when the concentration of acetylcysteine was in the range of 1.0 mg/mL to 1.5 mg/mL and the concentration of sodium citrate was 2.0 mg/mL, the individual impurity was 0.2% or less while the total impurity was 1.0% or less (Examples 8 and 10), thus showing excellent stability. However, when the concentration of acetylcysteine was lower than the 1.0~1.5 mg/mL, a change in the appearance (discoloration) occurred although the impurity content satisfied the acceptance criteria (Examples 1 and 2).

Additionally, when the concentration of acetylcysteine was 2.0 mg/mL and the concentration of sodium citrate was 5.0 mg/mL, the impurity level satisfied the acceptance criteria but a change in the appearance (discoloration) occurred (Example 13).

Additionally, when the concentration of acetylcysteine was 0.5 mg/mL and the concentration of sodium citrate was in the range of 1.0 mg/mL to 1.5 mg/mL, the impurity level satisfied the acceptance criteria but a change in the appearance (discoloration) occurred (Examples 3 to 7).

TABLE 9

| | Conc. of active ingredient (mg/mL) | Antioxidant | Conc. of antioxidant (mg/mL) | Buffering agent | Conc. of buffering agent (mg/mL) | pH | | Impurities (%) individual/total |
|---|---|---|---|---|---|---|---|---|
| Ex. 15 | 25 | acetylcysteine | 1.5 | sodium citrate | 5.0 | 6.9 | initial | 0.16/0.2 (colorless and transparent) |

TABLE 9-continued

| | Conc. of active ingredient (mg/mL) | Antioxidant | Conc. of antioxidant (mg/mL) | Buffering agent | Conc. of buffering agent (mg/mL) | pH | | Impurities (%) individual/total |
|---|---|---|---|---|---|---|---|---|
| | | | | | | | week 2 | 0.18/0.2 (colorless and transparent) |
| | | | | | | | week 4 | 0.17/0.3 (colorless and transparent) |
| Ex. 16 | 25 | acetylcysteine | 1.5 | sodium citrate | 5.0 | 7.2 | initial | 0.14/0.2 (colorless and transparent) |
| | | | | | | | week 2 | 0.15/0.3 (colorless and transparent) |
| | | | | | | | week 4 | 0.14/0.2 (colorless and transparent) |
| Ex. 11 | 25 | acetylcysteine | 1.5 | sodium citrate | 5.0 | 7.5 | initial | 0.07/0.1 (colorless and transparent) |
| | | | | | | | week 2 | 0.10/0.1 (colorless and transparent) |
| | | | | | | | week 4 | 0.11/0.2 (colorless and transparent) |

As can be confirmed in the results of Table 9 above, when both acetylcysteine as an antioxidant and sodium citrate as a buffering agent were used together in the formulations, in spite of changes in pH, individual impurity was 0.2% or less while the total impurity was 1.0% or less during the four week stability test period under stress testing conditions, thus showing excellent stability.

TABLE 10

| | Conc. of active ingredient (mg/mL) | Antioxidant | Conc. of antioxidant (mg/mL) | Buffering agent | Conc. of buffering agent (mg/mL) | pH | Oxygen gas content within the headspace (v/v %) | | Impurities (%) individual/total |
|---|---|---|---|---|---|---|---|---|---|
| Ex. 17 | 25 | acetylcysteine | 1.5 | sodium citrate | 5.0 | 7.4 | 3 | initial | ≤0.05/0.0 (colorless and transparent) |
| | | | | | | | | week 2 | ≤0.05/0.0 (colorless and transparent) |
| | | | | | | | | week 4 | ≤0.05/0.0 (colorless and transparent) |
| Ex. 18 | 25 | acetylcysteine | 1.5 | sodium citrate | 5.0 | 7.4 | 5 | initial | ≤0.05/0.0 (colorless and transparent) |
| | | | | | | | | week 2 | 0.12/0.4 (colorless and transparent) |
| | | | | | | | | week 4 | 0.22/0.7 (colorless and transparent) |
| Ex. 19 | 25 | acetylcysteine | — | sodium citrate | — | 7.4 | 3 | initial | ≤0.05/0.0 (colorless and transparent) |
| | | | | | | | | week 2 | 0.18/0.7 (pale yellow) |
| | | | | | | | | week 4 | 0.57/1.5 (yellow) |
| Ex. 20 | 25 | acetylcysteine | — | sodium citrate | — | 7.4 | 5 | initial | ≤0.05/0.0 (colorless and transparent) |
| | | | | | | | | week 2 | 0.25/0.8 (pale yellow) |
| | | | | | | | | week 4 | 0.61/1.8 (yellow) |

If the above formulation is manufactured via large-scale production for commercialization, the opportunity for the formulation to contact oxygen, which is the main cause of the generating impurities, may be increased. To prevent the contact with oxygen, the stability of formulations could be secured by controlling the oxygen gas content remaining in the manufacturing process.

As can be confirmed from the results of Table 10 above, when both acetylcysteine as an antioxidant and sodium citrate as a buffering agent were used together in the formulations, the total amount of impurities in the formulations was shown to be reduced by controlling the oxygen gas content within the headspace compared to the level conventionally manufactured (Example 11), thus showing excellence in stability (Examples 17 and 18). In particular, when the oxygen gas content within the headspace was controlled at a level of 3 v/v % or less, the individual impurity was 0.2% or less while the total impurity was 1.0% or less during the four weeks' stability test period under stress testing conditions, thus showing excellent stability (Example 17).

Even when an antioxidant was not added, it was confirmed that the formulation stability was secured until the first two weeks under stress testing conditions when the oxygen gas content within the headspace was maintained at a level of 3 v/v % or less (Example 19), compared to when the oxygen gas content within the headspace was not controlled (Comparative Example 1). Through the results above, it was confirmed that the regulation of the oxygen gas content within the headspace can contribute to the improvement of formulation stability. However, when an antioxidant and a buffering agent were additionally added to the formulation (Examples 17 and 18), more complete stability was secured.

TABLE 11

| | Conc. of active ingredient (mg/mL) | Type of antioxidant | Conc. of antioxidant (mg/mL) | pH | | Impurities (%) Individual/Total |
|---|---|---|---|---|---|---|
| Comp. Ex. 1 | 25 | — | — | 7.5 | initial | 0.01/0.1 |
| | | | | | week 2 | 0.33/0.8 |
| | | | | | week 4 | 0.66/2.1 |
| Comp. Ex. 2 | 25 | ascorbic acid | 0.3 | 6.5 | initial | 0.63/0.7 |
| | | | | | week 2 | 0.6/1.0 |
| | | | | | week 4 | N.A. (appearance unsatisfied) |
| Comp. Ex. 3 | 25 | sodium thiosulfate | 0.3 | 7.5 | initial | 0.04/0.2 |
| | | | | | week 2 | 0.24/0.6 |
| | | | | | week 4 | 0.72/1.7 |
| Comp. Ex. 4 | 25 | butylated hydroxyanisole | 0.3 | 9.9 | initial | 0.1/0.3 |
| | | | | | week 2 | 0.45/1.3 |
| | | | | | week 4 | N.A. (appearance unsatisfied) |
| Comp. Ex. 5 | 25 | propyl gallate | 0.3 | 9.5 | initial | 0.11/0.4 |
| | | | | | week 2 | 1.03/2.7 |
| | | | | | week 4 | N.A. (appearance unsatisfied) |
| Comp. Ex. 6 | 25 | EDTA | 0.3 | 6.5 | initial | 0.53/2.7 |
| | | | | | week 2 | 1.23/3.0 |
| | | | | | week 4 | N.A. (appearance unsatisfied) |
| Comp. Ex. 7 | 25 | L-cysteine | 0.3 | 7.5 | initial | 0.05/0.2 |
| | | | | | week 2 | 0.38/1.0 |
| | | | | | week 4 | 0.71/1.8 |
| Comp. Ex. 8 | 25 | L-methionine | 0.3 | 7.4 | initial | 0.05/0.2 |
| | | | | | week 2 | 0.35/0.9 |
| | | | | | week 4 | 0.51/1.3 |

As can be confirmed from the results of Table 11 above, when a conventionally used antioxidant was used in the formulations, there were changes in the appearance of the formulation, such as precipitation or discoloration, or increases of at least 0.2% in individual impurity and at least 1.0% in total impurity during the stability test period under stress conditions. Accordingly, it was confirmed that when pemetrexed-comprising liquid formulations for injection were prepared using an antioxidant for conventional use, the formulations showed inappropriate stabilities in terms of impurities, changes in their appearance, etc.

TABLE 12

| | Conc. of active ingredient (mg/mL) | Type of antioxidant | Conc. of antioxidant (mg/mL) | Buffering agent | Conc. of buffering agent (mg/mL) | pH | | Impurities (%) Individual/Total |
|---|---|---|---|---|---|---|---|---|
| Comp. Ex. 9 | 25 | — | — | sodium citrate | 1.5 | 7.4 | initial | 0.15/0.2 (colorless and transparent) |
| | | | | | | 7.4 | week 2 | 0.13/0.6 (deep yellow) |
| | | | | | | — | week 4 | N.A. (appearance unsatisfied) |
| Comp. Ex. 10 | 25 | — | — | sodium citrate | 2.0 | 7.3 | initial | 0.03/0.0 (colorless and transparent) |
| | | | | | | 7.0 | week 2 | 0.11/0.3 (deep yellow) |
| | | | | | | 7.0 | week 4 | 0.17/0.5 (deep yellow) |
| Ex. 11 | 25 | acetylcysteine | 1.5 | sodium citrate | 5.0 | 7.5 | initial | 0.07/0.1 (colorless and transparent) |
| | | | | | | 7.3 | week 2 | 0.10/0.1 (colorless and transparent) |
| | | | | | | 7.2 | week 4 | 0.11/0.2 (colorless and transparent) |
| Comp. Ex. 11 | 25 | acetylcysteine | 0.5 | — | — | 7.2 | initial | 0.12/0.1 (colorless and transparent) |
| | | | | | | 6.9 | week 2 | 0.14/0.3 (pale yellow) |
| | | | | | | 6.9 | week 4 | 0.15/0.5 (pale yellow) |
| Ex. 8 | 25 | acetylcysteine | 0.5 | sodium citrate | 5.0 | 7.4 | initial | 0.07/0.1 (colorless and transparent) |
| | | | | | | 7.1 | week 2 | 0.10/0.2 (colorless and transparent) |
| | | | | | | 7.1 | week 4 | 0.12/0.5 (pale yellow) |
| Comp. Ex. 12 | 25 | acetylcysteine | 1.5 | — | — | 7.5 | initial | 0.09/0.1 (colorless and transparent) |
| | | | | | | 7.1 | week 2 | 0.12/0.3 (colorless and transparent) |
| | | | | | | 7.0 | week 4 | 0.12/0.3 (light pale yellow) |
| Comp. Ex. 13 | 25 | L-cysteine | 0.5 | — | — | 7.5 | initial | 0.12/0.2 (colorless and transparent) |
| | | | | | | 6.9 | week 2 | 0.12/0.2 (pale yellow and abnormal odor) |
| | | | | | | 6.9 | week 4 | 0.12/0.3 (pale yellow) |
| Comp. Ex. 14 | 25 | L-cysteine | 1.5 | — | — | 7.5 | initial | 0.09/0.1 (colorless and transparent) |
| | | | | | | 7.4 | week 2 | 0.11/0.1 (abnormal odor) |
| | | | | | | 7.2 | week 4 | 0.12/0.2 (abnormal odor) |

As can be confirmed from the results of Table 12 above, when both acetylcysteine as an antioxidant and sodium citrate as a buffering agent were used together in the formulations, and preferably when the concentration of acetylcysteine was 1.5 mg/mL and the concentration of sodium citrate was 5.0 mg/mL, the formulations showed the individual impurity of 0.2% or less and the total impurity of 1.0% or less during the four weeks' stability test period under stress testing conditions, thus showing excellent stabilities (Example 11).

In contrast, when only sodium citrate, a buffering agent, was used, the color of the solutions began to turn deep yellow from the second week stress testing conditions (Comparative Examples 9 and 10). Additionally, when only L-cysteine and acetylcysteine, an antioxidant, were used, the color of the solutions began to turn pale yellow from the second week under stress testing conditions, and their pH decreased significantly during the four weeks stress testing conditions (Comparative Examples 11, and 12 to 14). That is, it was confirmed that when both acetylcysteine and sodium citrate were used simultaneously, the stability of impurities was significantly improved, unlike when acetylcysteine or sodium citrate was used alone.

Additionally, the formulations of Comparative Examples 13 and 14, which were prepared using only L-cysteine, produced an abnormal odor, such as a foul odor of rotten eggs, from the second week under the stress testing conditions. However, such abnormal odor was not generated in the formulations constituted according to the present invention, thus showing the improvement of the present invention.

TABLE 13

| | Conc. of active ingredient (mg/mL) | Type of antioxidant | Conc. of antioxidant (mg/mL) | Buffering agent | Conc. of buffering agent (mg/mL) | pH | | Impurities (%) Individual/Total |
|---|---|---|---|---|---|---|---|---|
| Ex. 11 | 25 | acetylcysteine | 1.5 | sodium citrate | 5.0 | 7.5 | initial | 0.07/0.1 (colorless and transparent) |
| | | | | | | 7.3 | week 2 | 0.10/0.1 (colorless and transparent) |
| Comp. Ex. 15 | 25 | acetylcysteine | 1.5 | sodium acetate | 5.0 | 7.4 | initial | 0.89/1.45 (pale yellow) |
| | | | | | | 7.1 | week 2 | 0.86/2.3 (deep yellow) |
| Comp. Ex. 16 | 25 | acetylcysteine | 1.5 | sodium hydrogen phosphate | 5.0 | 7.5 | initial | 0.23/0.2 (colorless and transparent) |
| | | | | | | 7.4 | week 2 | 0.21/0.9 (yellow) |
| Comp. Ex. 17 | 25 | acetylcysteine | 1.5 | potassium dihydrogen phosphate | 5.0 | 7.5 | initial | 0.24/0.2 (colorless and transparent) |
| | | | | | | 7.2 | week 2 | 0.23/0.8 (light pale yellow) |

As can be confirmed from the results of Table 13 above, when acetylcysteine as an antioxidant was used along with various kinds of buffering agents for general use in the formulations to examine the resulting stabilities, there were observed changes in appearance (discoloration) from the initial stage or an increase of at least 0.2% of individual impurity and at least 1.0% of total impurity for those comprising the buffering agents other than sodium citrate.

Accordingly, it was confirmed that, in preparing pemetrexed-comprising liquid formulations for injection, the most excellent stability of the formulations could be achieved only when both acetylcysteine as an antioxidant and sodium citrate as a buffering agent were used together.

Experimental Example 2

Accelerated Stability Test (40° C./70%, 4 Month Evaluation of Stability)

The results of accelerated stability tests performed are shown in Table 14.

TABLE 14

| | Conc. of active ingredient (mg/mL) | Type of antioxidant | Conc. of antioxidant (mg/mL) | Buffering agent | Conc. of buffering agent (mg/mL) | pH | | Impurities (%) Individual/Total |
|---|---|---|---|---|---|---|---|---|
| Ex. 11 | 25 | acetylcysteine | 1.5 | sodium citrate | 5.0 | 7.5 | initial | 0.07/0.1 (colorless and transparent) |

TABLE 14-continued

| | Conc. of active ingredient (mg/mL) | Type of antioxidant | Conc. of antioxidant (mg/mL) | Buffering agent | Conc. of buffering agent (mg/mL) | pH | | Impurities (%) Individual/Total |
|---|---|---|---|---|---|---|---|---|
| | | | | | | 7.3 | month 2 | 0.10/0.1 (colorless and transparent) |
| | | | | | | 7.3 | month 4 | 0.14/0.2 (colorless and transparent) |
| | | | | | | 7.2 | month 6 | 0.18/0.4 (light pale yellow) |
| Comp. Ex. 1 | 25 | — | — | — | — | 7.5 | initial | 0.01/0.1 |
| | | | | | | — | month 2 | 0.04/0.1 (yellow) |
| | | | | | | — | month 4 | 0.60/1.5 (yellow) |
| Comp. Ex. 12 | 25 | acetylcysteine | 1.5 | — | — | 7.5 | initial | 0.09/0.1 (colorless and transparent) |
| | | | | | | 7.1 | month 4 | 0.33/0.8 (colorless and transparent) |
| Comp. Ex. 14 | 25 | L-cysteine | 1.5 | — | — | 7.5 | initial | 0.09/0.1 (colorless and transparent) |
| | | | | | | 7.2 | month 4 | 0.12/0.2 (colorless, transparent, and abnormal odor) |

As can be confirmed from the results of Table 14 above, the formulations of Comparative Example 1, which were prepared using only water for injection as a carrier without any antioxidant, began to turn yellow from the second month under the accelerated condition, and showed an individual impurity of 0.2% or higher and a total impurity of 1.0% or higher on the fourth month under the accelerated condition, and were thus not appropriate in terms of stability. However, the formulations prepared in Example 11, which were prepared using both acetylcysteine as an antioxidant and sodium citrate as a buffering agent, showed an individual impurity of 0.2% or less and a total impurity of 1.0% or less, thus showing excellent stability during the six-month stability test period under accelerated condition.

In contrast, the formulations prepared using only acetylcysteine as an antioxidant (Comparative Example 12) also began to turn yellow or showed an individual impurity of 0.2% or higher from the fourth month under accelerated condition, and were thus not appropriate in terms of stability.

Additionally, the formulations containing only L-cysteine prepared in Comparative Example 14 satisfied the acceptance criteria regarding to an impurity but produced an abnormal odor similar to the odor of rotten eggs from the fourth month under accelerated condition. However, the formulations prepared according to the present invention, i.e., those prepared in Example 11, did not produce such abnormal odor.

The invention claimed is:

1. A pemetrexed formulation filled in a sealed container comprising pemetrexed or a pharmaceutically acceptable salt thereof as an active ingredient, N-acetyl-L-cysteine and sodium citrate, wherein the formulation comprises an oxygen gas content of 3 v/v % or less within the headspace of the container, relative to the total volume of the headspace.

2. The pemetrexed formulation of claim 1, wherein the concentration ratio of the pemetrexed or a pharmaceutically acceptable salt thereof, N-acetyl-L-cysteine, and sodium citrate is 1 to 30:0.15 to 2.0:1.0 to 15.0.

3. The pemetrexed formulation of claim 2, wherein the concentration ratio of the pemetrexed or a pharmaceutically acceptable salt thereof, N-acetyl-L-cysteine, and sodium citrate is 1 to 30:1.5:1.0 to 15.0.

4. The pemetrexed formulation of claim 1, wherein the formulation is a liquid formulation storable in the state of a solution.

5. The pemetrexed formulation of claim 1, wherein the formulation is a liquid formulation for injection filled in a sealed, ready-to-use container.

6. The pemetrexed formulation of claim 1, wherein the oxygen gas content is adjusted by substituting the oxygen gas within the headspace of the container with an inert gas.

7. The pemetrexed formulation of claim 6, wherein the inert gas is nitrogen gas or argon gas.

\* \* \* \* \*